(12) United States Patent
Reustle (10) Patent No.: US 7,453,365 B2
(45) Date of Patent: *Nov. 18, 2008

(54) SYSTEM AND METHOD FOR ELIMINATION OF BEDWETTING BEHAVIOR

(75) Inventor: M. Charles Reustle, Corpus Christi, TX (US)

(73) Assignee: BreakPoint Solutions, Inc., Corpus Christi, TX (US)

( * ) Notice: Subject to any disclaimer, the term of this patent is extended or adjusted under 35 U.S.C. 154(b) by 5 days.

This patent is subject to a terminal disclaimer.

(21) Appl. No.: 11/789,465

(22) Filed: Apr. 24, 2007

(65) Prior Publication Data

US 2008/0030349 A1 Feb. 7, 2008

Related U.S. Application Data

(63) Continuation of application No. 11/121,702, filed on May 4, 2005, now Pat. No. 7,209,044.

(60) Provisional application No. 60/568,099, filed on May 4, 2004.

(51) Int. Cl.
*G08B 23/00* (2006.01)
(52) U.S. Cl. ............. 340/573.5; 340/573.1; 340/539.12
(58) Field of Classification Search ............. 340/573.5, 340/573.1, 539.12, 309.16, 309.7; 600/300; 128/903
See application file for complete search history.

(56) References Cited

U.S. PATENT DOCUMENTS

| | | | |
|---|---|---|---|
| 3,778,570 A | 12/1973 | Shuman | |
| 4,271,406 A | 6/1981 | Wilson | |
| 4,316,273 A | 2/1982 | Jetter | |
| 4,347,503 A | 8/1982 | Uyehara | |
| 4,356,479 A | 10/1982 | Wilson | |
| 4,800,370 A | 1/1989 | Vetecnik | |
| 4,852,854 A | 8/1989 | Peng et al. | |
| 4,853,854 A * | 8/1989 | Behar et al. | 368/10 |
| 5,043,704 A | 8/1991 | Blakeney | |
| 5,074,317 A | 12/1991 | Bondell et al. | |
| 5,144,284 A | 9/1992 | Hammett | |
| 5,341,127 A | 8/1994 | Smith | |
| 5,365,496 A | 11/1994 | Tolan-Samilow | |
| 5,929,747 A | 7/1999 | Rosenblatt et al. | |
| 6,072,384 A | 6/2000 | Baker | |
| 6,097,297 A | 8/2000 | Fard | |
| 6,211,787 B1 | 4/2001 | Yoshiike et al. | |
| D452,221 S | 12/2001 | Garza | |
| 6,784,797 B2 | 8/2004 | Smith et al. | |
| 7,027,358 B1 | 4/2006 | Esposito et al. | |
| 7,209,044 B2 * | 4/2007 | Reustle | 340/573.1 |

* cited by examiner

*Primary Examiner*—John A Tweel, Jr.
(74) *Attorney, Agent, or Firm*—Kammer Browning PLLC (57) ABSTRACT

A system and method for facilitating the elimination of bedwetting behavior utilizing a number of RF transceivers which include a base unit, an alarm unit, and a remote keypad unit. The method works through programmed sleep interruption based upon a user's previously established sleep and bedwetting pattern.

15 Claims, 10 Drawing Sheets

| Arousal Time Settings – Modification Rules | | |
|---|---|---|
| Condition at Alarm | Condition at Morning | Action |
| WET | DRY | move alarm earlier |
| DRY | WET | move alarm later or add additional alarm or both |
| DRY | DRY | move alarm later or eliminate an alarm or both |
| WET | WET | move alarm earlier and add additional alarm |

FIG. 5C

BREAKPOINT PROGRAM
Daily progress tracking

Date-_____________    Day-_____________

Patient -_____________    Patient Age -_____

BEDTIME - _________________ (Must be strictly enforced)

FIRST WAKE-UP -  _______________
SECOND WAKE-UP -  _____________
THIRD WAKE – UP -_____________
FOURTH WAKE-UP-_____________

Did Parent or Guardian Assist in wake-up procedures?-
Y or NO

PROTECTIVE CLOTHING UTILIZED -   Y or NO

Was Evening a success?_____________________

GENERAL NOTES / OBSERVATIONS / INSIGHTS_______
_______________________________________________
_______________________________________________
_______________________________________________
_______________________________________________
_______________________________________________
_______________________________________________
_______________________________________________

FIG. 6A

Week #1

BREAKPOINT PROGRAM
Daily progress tracking

Date -   7/21/03     Day -   Monday

Patient -   Thomas R.     Patient Age -   15+

BEDTIME -   10:30 pm - Prep
            11:00 pm - Lights Out (Must be strictly enforced)

FIRST WAKE-UP -     12:00 am
SECOND WAKE-UP -    3:00 am
THIRD WAKE – UP -________________
FOURTH WAKE-UP-________________

Did Parent or Guardian Assist in wake-up procedures?-
            Y or NO

PROTECTIVE CLOTHING UTILIZED -   Y or NO

Was Evening a success? Alarm worked properly. Patient wet between 7:00 am – 8:00 am after being awoken and allowed to make choice – bad parent choice.

GENERAL NOTES / OBSERVATIONS / INSIGHTS:

Thomas very tired – went right to sleep. Drank 2 -3 sodas 1 hour before bed.
2nd wake-up required to heavy fluid intake.
Thomas chose not to have another wake-up until 7:00 am. Results will determine tomorrow's wake-up times. Changed mind – added 3:00 am wake-up. Patient wet after being woken at 7:00 am, but allowed to make choice of whether to get up and use bathroom. Parent will now decide.

Alarm Notes: Battery changed in key pad.
- Add night light feature to adult unit
- Adjustable volume alarm on both units
- Remote unit to have multiple sounds and volume control

FIG. 6B

BREAKPOINT PROGRAM
Daily progress tracking

Date - <u>7/22/03</u>  Day - <u>Tuesday</u>

Patient – <u>Thomas R.</u>  Patient Age – <u>15+</u>

BEDTIME – <u>10:00 pm - Prep</u>
<u>11:00 pm - Lights Out</u> (Must be strictly enforced)

FIRST WAKE-UP -   <u>12:30 am</u>
SECOND WAKE-UP -   <u>3:30 am</u>
THIRD WAKE – UP -   <u>6:30 am</u>
FOURTH WAKE-UP-\_\_\_\_\_\_\_\_\_\_\_\_

Did Parent or Guardian Assist in wake-up procedures?-
<u>Y</u> or NO

PROTECTIVE CLOTHING UTILIZED -   Y or <u>NO</u>

Was Evening a success? <u>Unit worked. No bedwetting at all.</u>

GENERAL NOTES / OBSERVATIONS / INSIGHTS:
<u>12:30 pm went great. Thomas used bathroom. Alarm went well.</u>
<u>3:30 am – Alarm worked – Tom was at keypad without assistance or help to wake up.</u>
<u>6:30 am – Alarm okay as set. Tom up and at keypad with no help. No bedwetting again and used bathroom each time on his own.</u>

FIG. 6C

BREAKPOINT PROGRAM
Daily progress tracking

Date -   7/28/03         Day -   Monday

Patient -   Thomas R.      Patient Age -   15+

BEDTIME –   10:00 pm – T.V. off/rest
10:30 pm - Lights Out (Must be strictly enforced)

FIRST WAKE-UP -     12:30 am – 2 hours
SECOND WAKE-UP -    3:30 am – reset to 3 hours
THIRD WAKE – UP -   6:30 am – work day wake up
FOURTH WAKE-UP - ___________

Did Parent or Guardian Assist in wake-up procedures?- Y or NO

PROTECTIVE CLOTHING UTILIZED -   Y or NO

Was Evening a success?  Yes! Yes! Yes!

GENERAL NOTES / OBSERVATIONS / INSIGHTS:
Moved alarm nearer to bed and tested.
Thomas chose to be in bed with lights out at 10:00 pm.
Parent chose to remain at 12:30 wake-up.
12:30 am wake-up – No problem. Thomas was up at panel and used bathroom.
3:30 pm – Thomas got up without assistance and used bathroom on own.
6:30 am – Thomas up on his own.

FIG. 6D

SYSTEM AND METHOD FOR ELIMINATION OF BEDWETTING BEHAVIOR

CROSS REFERENCE TO CORRESPONDING APPLICATIONS

This application is a Continuation of U.S. patent application Ser. No. 11/121,702, filed on May 4, 2005, now U.S. Pat. No. 7,209,044, issued on Apr. 24, 2007, which claims the benefit under Title 35 United States Code §119(e) of U.S. Provisional Application No. 60/568,099 filed May 4, 2004.

BACKGROUND OF THE INVENTION

1. Field of the Invention

The present invention relates generally to systems and methods for bedwetting detection and prevention. The present invention relates more specifically to a system and method utilizing a remote wireless alarm unit for behavior modification to eliminate bedwetting.

2. Description of the Related Art

The basic bedwetting prevention system utilized in homes, hospitals, and extended care facilities provides a number of essential elements intended to detect the condition and to transmit and receive a signal to alert either the user and/or the caregiver. Many of the currently available systems are designed simply to alert a caregiver in order to minimize the time that the user must remain in wet bedding and clothing. Other currently available systems disclose devices designed to wake the user upon activation of the wetness sensor. The basic existing system incorporates a fluid sensor, a sensor signal transmitter, and a signal receiver alarm unit. There is typically a switch which operates to deactivate the system. There is also typically a remote receiver designed to alert a parent or a caregiver. In addition, most bedwetting systems are directed to detection of moisture and dry skin maintenance rather than a behavior modification program to eliminate bedwetting altogether.

For successful integration of a behavior modification program with a bedwetting elimination system, the alarm receiver unit must thoroughly wake the user and the deactivation mechanism must require sufficient alertness to enable reprogramming of the user's sleep patterns and behavior. Various prior art devices require a simple physical response to deactivate the alarm such as flipping a switch, but such actions can often be performed by the user without arousal to the point of mental consciousness. Because behavior modification requires alteration of stimuli/response patterns, optimal reprogramming of sleep and bedwetting patterns will occur most easily if the user attains a certain minimum level of mental consciousness.

Efforts have been made in the past to appropriately rouse the user to facilitate such learning and training. For the most part these efforts have focused on the loudness of the alarm or the requirement that the user perform a simple physical motion to deactivate the alarm. Such systems clearly suffer from the inability to maintain the association between the bedwetting event and the interruption of sleep over time. This is due to the likelihood of the user learning to perform the simple physical motion without sufficient mental consciousness to "reprogram" the bedwetting behavior.

Several patents in the prior art disclose systems designed to detect bedwetting and transmit a signal which triggers an alarm at a remote location. U.S. Pat. No. 4,800,370 issued to Vetecnik on Jan. 24, 1989 entitled WETNESS DETECTION SYSTEM, U.S. Pat. No. 4,271,406 issued to Wilson on Jun. 2, 1981 entitled BED WETTING TATTLER, and U.S. Pat. No. 6,097,297 issued to Fard on Aug. 1, 2000 entitled WETNESS AWARENESS TRAINING DEVICE teach systems primarily directed to alerting a parent or caregiver, rather than the individual in the bed, to the bedwetting condition.

Other prior art patents are designed to detect bedwetting and awaken the user. Examples of these include U.S. Pat. No. 4,347,503 issued to Uyehara on Aug. 31, 1982 entitled BEDWETTING DETECTION DEVICE, U.S. Pat. No. 3,778,570 issued to Shuman on Dec. 11, 1973 entitled ENURESIS BED PAD, and U.S. Pat. No. 5,074,317 issued to Bondell et al. on Dec. 24, 1991 entitled SYSTEM FOR TREATMENT OF ENURESIS. These inventions detect moisture and awaken the user. Uyehara teaches a moisture-sensitive device which triggers an alarm to awaken the user, whereupon the user must turn off the device by flipping a switch located on a bedside control box. Shuman discloses a bed pad with sensor strips that form a circuit when enuresis occurs, resulting in activation of an audible and/or visual signal to awaken the user. No deactivation process is disclosed. Bondell et al. describes an interactive computerized training system which verbally rewards the user. The system includes a wireless moisture sensor that is clipped to the underpants of the user as well as a remote alarm deactivation key and a bedside system reset key.

U.S. Pat. No. 6,072,384 issued to Baker on Jun. 6, 2000 entitled BED WETTING PREVENTION SYSTEM, awakens the user and requires that the user be at a remote location, such as a bathroom, in order to insert a disc-shaped magnet into a radio assembly housing in order to silence the alarm and reset the system.

While many efforts have been made in the past to provide a system to detect bedwetting behavior, such efforts have generally failed to achieve the goal of training the user to stop bedwetting. It would be desirable to have a system and method for the elimination of bedwetting behavior that is based upon the user's bedwetting pattern and which requires sufficient interaction by the user for behavior modification to occur. It would further be desirable that the system be inexpensive to manufacture and easy to use.

SUMMARY OF THE INVENTION

It is therefore an object of the present invention to provide a system and method for use in eliminating bedwetting that simplifies the training and reprogramming of sleep patterns and behavior. The present invention includes components that are directed towards improving the means by which the system is deactivated without sacrificing the overall simplicity of the system. The goal is to achieve these improvements in such a manner that deactivation of the system by the user does not become an automatic response, thus bypassing the level of arousal required for behavior modification to occur. In addition, rather than being based on the detection of a bedwetting event, the present invention is based on the anticipation of such an event through an historical awareness of individual bedwetting patterns.

In fulfillment of these and other objectives, the system of the present invention provides three structural components: a wireless base unit, wireless remote alarm, and wireless remote keypad. The method of use of the present invention requires that the user enter a sequence of code characters in order to silence an alarm. The code entry is a complex mental task that ensures that the user is sufficiently alert to understand and learn. The code is written down and displayed at a remote location, such as the inside of a cabinet door, for easy reference in case the user forgets the code. The specific code is changed every few days to require sufficient user cognition and arousal for conscious learning to occur and to reduce the chance of rote keystroke operation. As discussed in detail below, the present invention has a carefully designed program of use which greatly enhances the likelihood of success.

The structural design of the system of the present invention also includes automatic nightlights to facilitate performance, battery back-up systems to eliminate interrupted function, and volume control circuitry for individualized loudness settings.

The base unit is designed to be located in a caregiver or parent's room or in a remote location other than the user's room. Specific arousal times are entered into this device to provide programmed arousal events based upon the user's established bedwetting pattern. An alarm alerts the caregiver and a remote signal activates a much louder alarm and night light in the user's room. This alarm can only be silenced by the user going into the remote location, i.e., bathroom, and keying in a sequence of code characters. The alarm unit also has a volume-controlled "sleep sound" generator to assist the user's return to sleep. The keypad is wireless, operates on a 9-volt battery, and has a backlit number panel designed for greater visibility in low lighting.

DETAILED DESCRIPTION OF THE PREFERRED EMBODIMENTS

Figure 1:
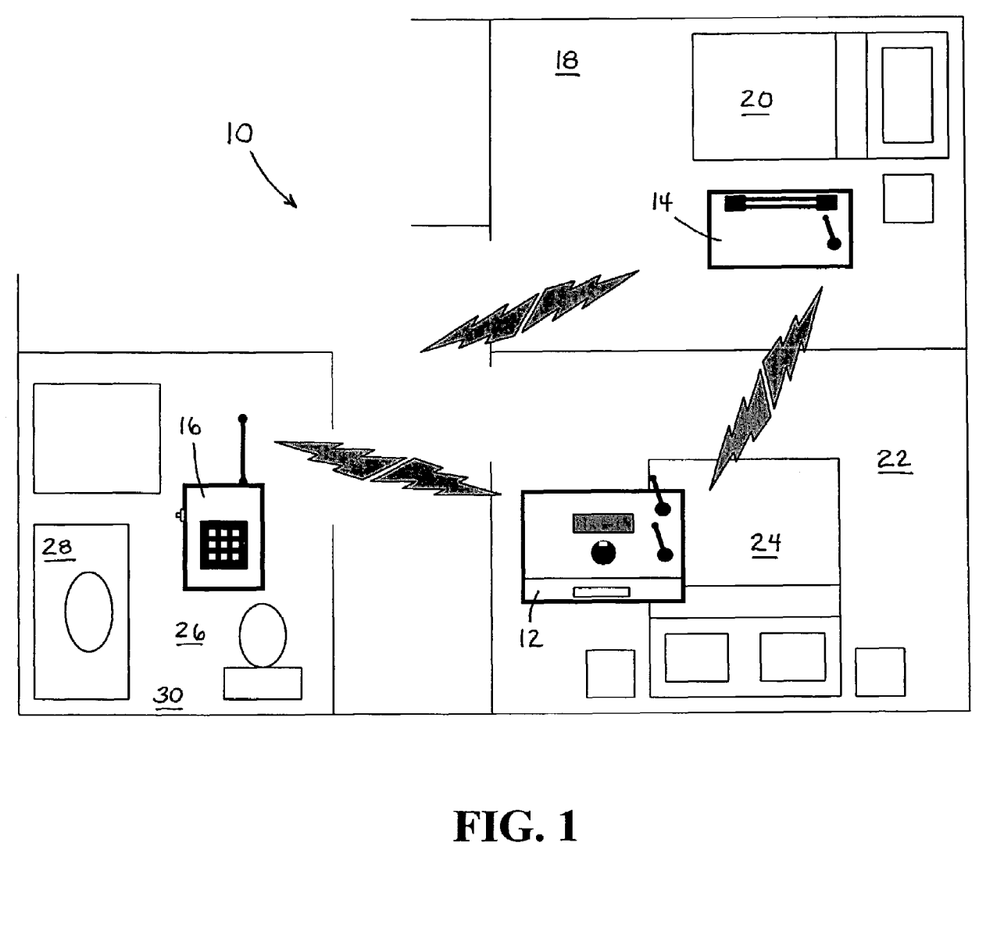
FIG. 1 is a schematic view of the structural components of the system for elimination of bedwetting behavior of the present invention.

Reference is made first to FIG. 1 for a general description of the structural components of the system for elimination of bedwetting behavior of the present invention. These components include the base unit, alarm unit, and keypad unit. The base unit hardware 12 for the bedwetting elimination system 10 is positioned in the parent or caregiver's room 22 next to the bed 24. The alarm unit 14 is located in the user's room 18, next to the user's bed 20. The keypad unit 16 is positioned in the bathroom 26 at a convenient mounting location 28. The code is also written down at a readily accessible code display reminder location 30.

Base unit 12, alarm unit 14, and keypad unit 16, each comprise low power radio frequency (RF) transceivers. Short distance, wireless signal communications occur between the base unit 12 and the alarm unit 14 as directed by the programmed timing in the base unit 12. Keypad unit 16 is capable of transmitting an alarm de-activation signal back to both base unit 12 and alarm unit 14. In an alternative embodiment, communication between these units may occur through a wired communication network.

Figure 2:
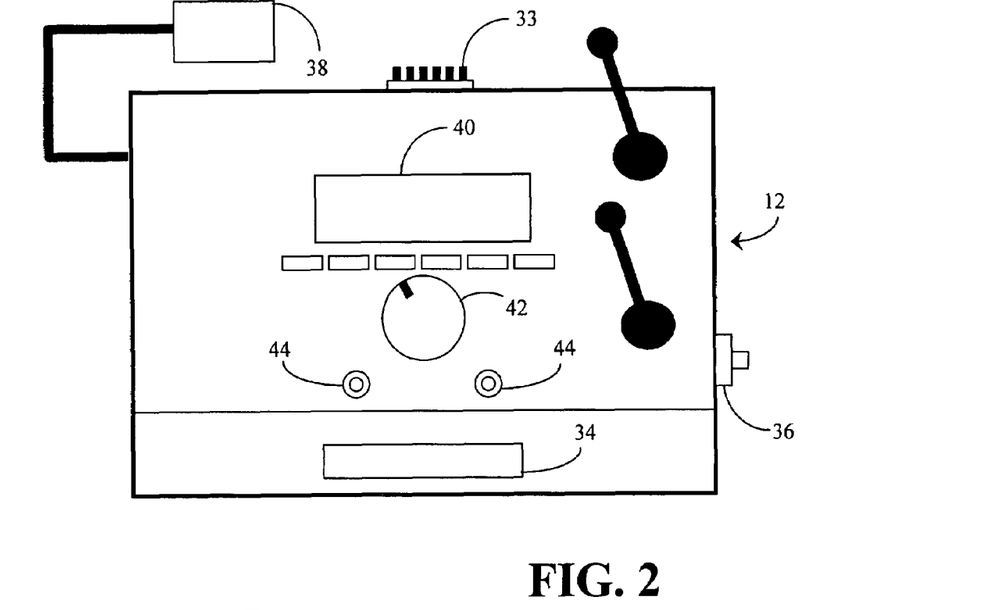
FIG. 2 is a top view of the wireless base unit of the present invention.

Reference is now made to FIG. 2 for a more detailed description of base unit 12 of the present invention. As described above, base unit 12 is designed to be located in the caregiver or parent's room 22 or in a remote location other than the user's room 18. The unit 12 allows the entry of at least six programmable time settings which are entered after developing the user's bedwetting behavior pattern. An automatic night light 34 turns on at the programmed alarm times and has a manual on/off switch 36. The base unit 12 utilizes 12 VDC through an AC adaptor 38 from the standard 110 VAC household current, with a 9-volt battery back-up system for use in the event of power failure. The unit has an internal alarm to awaken the caregiver. This alarm may have a volume control and an on/off switch (not shown). Indicator lights 44 show the power status of the unit (main power and 9V backup). The unit also functions as an LCD clock through LCD display 40 as is well known in the art. A DIP switch 33 is positioned on base unit 12 to allow user selection of a code number for communication between the units in the system. The alarm timing functions of base unit 12, which are selectable through rotary switch/selector knob 42, allow specific alarm/arousal times to be entered into the device, based upon the user's existing bedwetting behavior pattern. At these pre-set times, an alarm is activated in the base unit 12, thus alerting the caregiver, while at the same time sending an RF signal to the alarm unit 14 in the user's room 18. This signal activates a much louder alarm and night light in the alarm unit 14 in order to arouse the user.

Figure 3:
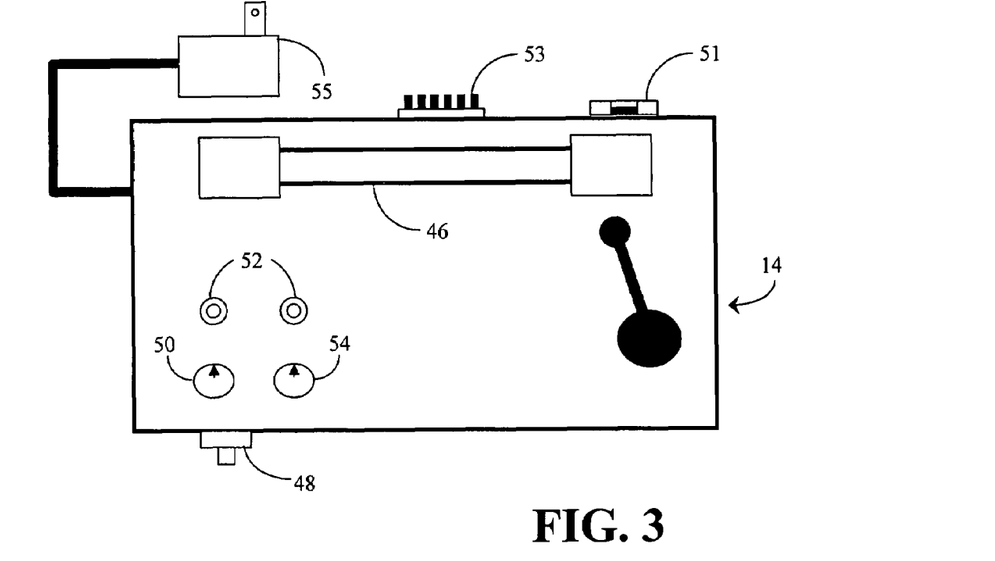
FIG. 3 is a top view of the remote wireless alarm unit of the present invention.

Reference is now made to FIG. 3 for a more detailed description of the remote wireless alarm unit 14 of the present invention. The remote alarm unit 14 is designed to be placed in the user's room 18 (FIG. 1). Upon activation by the base unit 12, as described above, the alarm unit 14 automatically turns on a night light 46 and emits a very loud alarm designed to awaken even the soundest of sleepers. The alarm can only be silenced by going into the remote location, i.e., bathroom 26 (FIG. 1), where the keypad unit 16 is installed.

The automatic night light 46 assists the user in seeing the path to the bathroom. The night light 46 may be manually controlled through on/off switch 48 such that the user can turn it off before returning to bed. Indicator lights 52 show the alarm status and the power status of the alarm unit. The alarm unit 14 also has a built-in "sleep sound" generator with volume control 50 and tone selection knob 54 that goes on for ten minutes after the night light 46 is turned off.

The alarm unit 14 may be attached to the wall of the user's room 18 by a Velcro®-type material and utilizes 12 VDC through an AC adaptor 55 from the standard 110 VAC household current power supply, with a 9-volt battery back-up in case of a power failure. The alarm unit 14 also incorporates a recessed (set screw) alarm volume control 51 in a relatively less accessible location on the back of the unit. A DIP switch 53 is likewise provided to allow user selection of a code number to facilitate communication between the units in the system.

Figure 4:
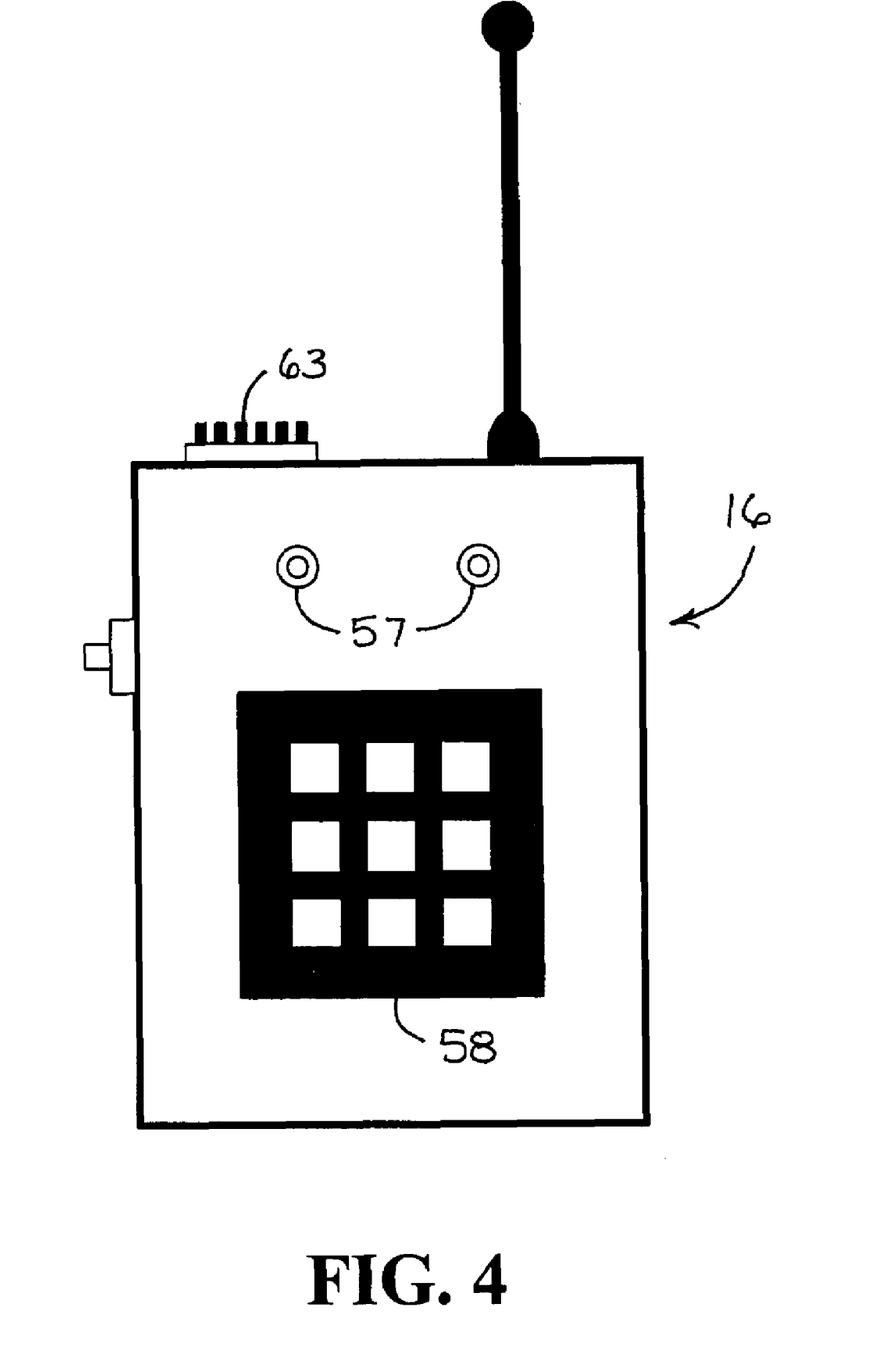
FIG. 4 is a top view of the remote wireless keypad unit of the present invention.

As illustrated in FIG. 4, the remote wireless keypad unit 16 of the present invention is designed so that the user must enter a sequence of code characters into keypad 58 to silence the alarms in both the remote alarm unit 14 and the base unit 12. Silencing of the alarm at the base unit 12 notifies the caregiver that the user has successfully entered the code at the remote keypad unit 16. This procedure ensures that the user is sufficiently awake to use the bathroom. In the preferred embodiment, the keypad unit 16 operates only through a 9-volt battery supply in order to minimize the possibility of electrical accident in a wet location, i.e., bathroom. The number panel of the keypad 58 is backlit in order to provide the user greater visibility without having to turn on a bright light in the bathroom 26 to silence the alarm. The backlighting is activated and deactivated with the alarm. The keypad unit 16 is attached to a mounting location 28 on the bathroom wall or mirror with a Velcro-type material. Power and alarm status indicators 57 are also provided on keypad unit 16. A DIP switch 63 is likewise provided on the unit as with the remote alarm unit 14 and the base unit 12.

The keypad unit 16 also provides the means whereby the alarm deactivation code may be programmed or reprogrammed into the system and is capable of communicating the code between all units in the system. Key selection programming as is well known in the art may be used to accomplish this function.

Figure 5A:
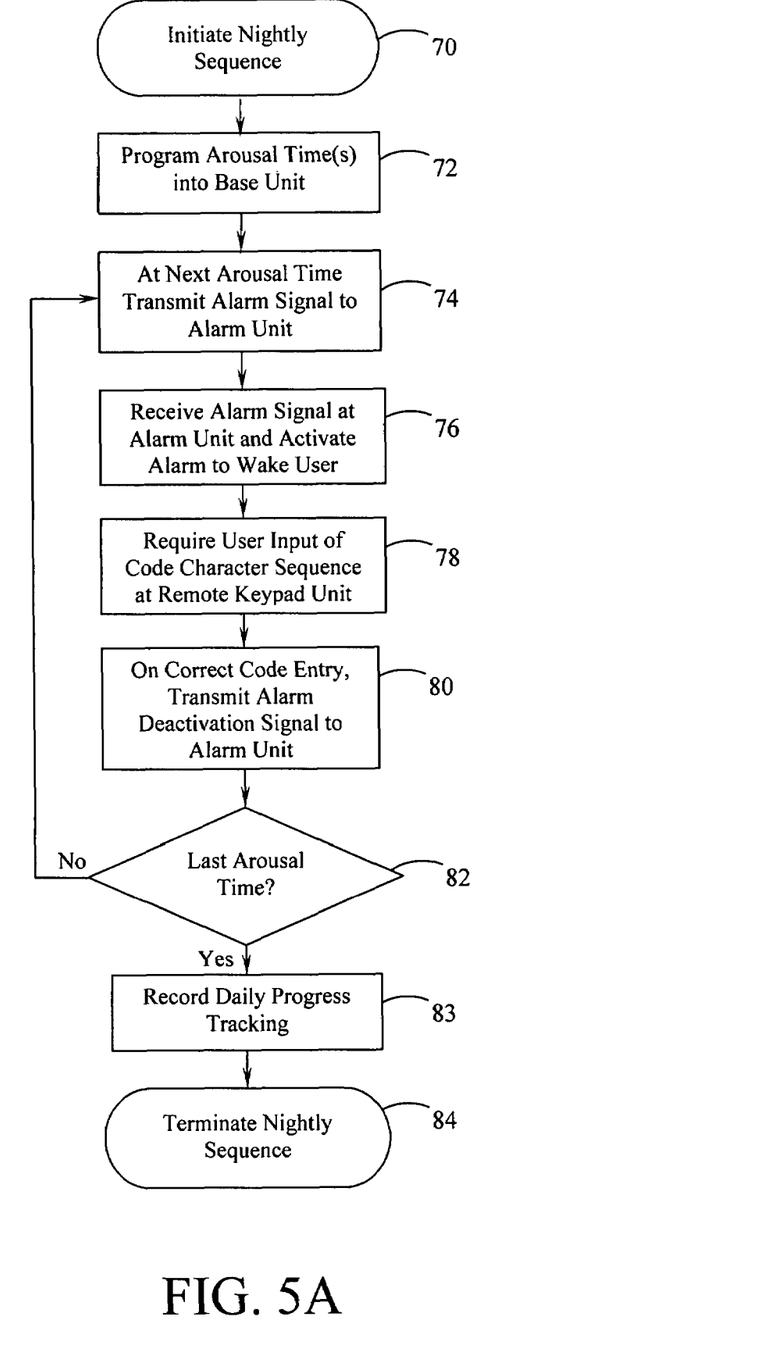
FIG. 5A is a flowchart of the nightly sequence method of use for the bedwetting elimination system of the present invention.
Figure 5B:
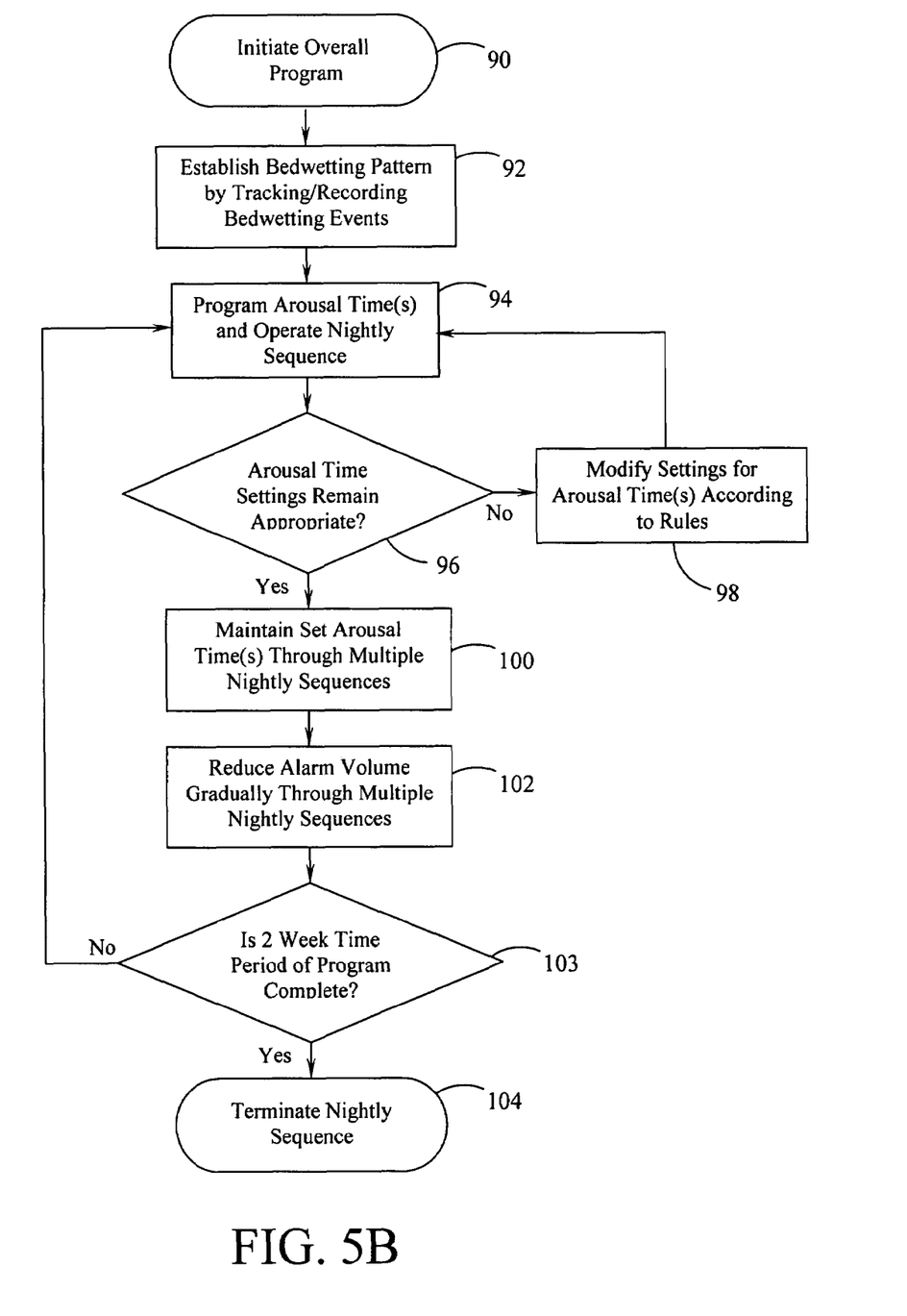
FIG. 5B is a flowchart of the overall program method of use for the bedwetting elimination system of the present invention.

Reference is now made to FIGS. 5A and 5B which provide flowcharts of the method of use for the bedwetting elimination system of the present invention. The method illustrated in FIG. 5A depicts the specific sequence of steps which occur on a nightly basis during the use of the system. FIG. 5B illustrates the sequence of steps for the overall program of behavior modification which is directed to reprogramming the user's sleep patterns and bedwetting behavior. If the user is currently using moisture sensing undergarments, the caregiver may already be aware of the user's bedwetting pattern. If so, the times coinciding with the user's pattern of bedwetting may be entered into the base unit 12 (step 92). If a bedwetting pattern has not been established, it is recommended that the user continue to use moisture resistant clothing. This period of time for continued use of moisture resistant clothing should not exceed one week.

The nightly sequence is initiated (step 70) by programming the arousal time(s) into the base unit (step 72). As the timer/clock in the base unit progresses to each programmed time, an alarm signal is transmitted to the alarm unit (step 74). This signal is received at the alarm unit and the alarm is activated (step 76). The user is required to go to the keypad unit and enter the code character sequence (step 78). On a correct code entry, the keypad unit transmits a deactivation signal to the alarm unit (and the base unit) (step 80). If this was the last programmed arousal time (step 82) the routine ends with a record of the nights events (step 83) as described in FIGS. 6A-6D, which terminates the nightly sequence (step 84). If further arousal times are programmed (step 82) the process returns to step 74 to continue the nightly sequence.

The user must have a strict bedtime schedule and stick with this schedule throughout the training program. This is to include weekends and holidays, during which time the bedtime may be later, but the scheduled waking pattern must be maintained. The scheduled morning wakeup time should be established with a sleeping schedule not to exceed eight hours.

No fluid intake should be allowed three hours before bedtime. The user may ingest a couple of ice cubes if absolutely necessary. Use of the bathroom prior to bedtime is critical in developing the user's bedwetting pattern. For the first two weeks of the program, the caregiver should awaken to assist the user with wakening and understanding the importance of using the bathroom and the keypad procedure for silencing the alarm. During the first two weeks, it is also crucial that the caregiver keep an accurate daily log (step 83). FIGS. 6A-6D illustrate sample daily progress tracking charts which are utilized to establish the user's sleeping and bedwetting pattern. As shown in FIGS. 6A-6D, the chart includes the bedtime and wake-up times plus general and specific details regarding the events of the evening, such as the degree of assistance from the caregiver.

The program starts the first night with a first wake up alarm two hours after bedtime regardless of whether the user fell asleep or not in that time frame. If the user is wet in the morning but not at the first wake up time, the first wake up is extended to three hours after bedtime (steps 96 and 98). This procedure is continued until the bedwetting pattern is established and programmed into the system (step 94). The objective is to limit the number of awakenings to once per night and no more than twice. This is accomplished by developing a schedule based upon individual bedwetting patterns.

Figure 5C:
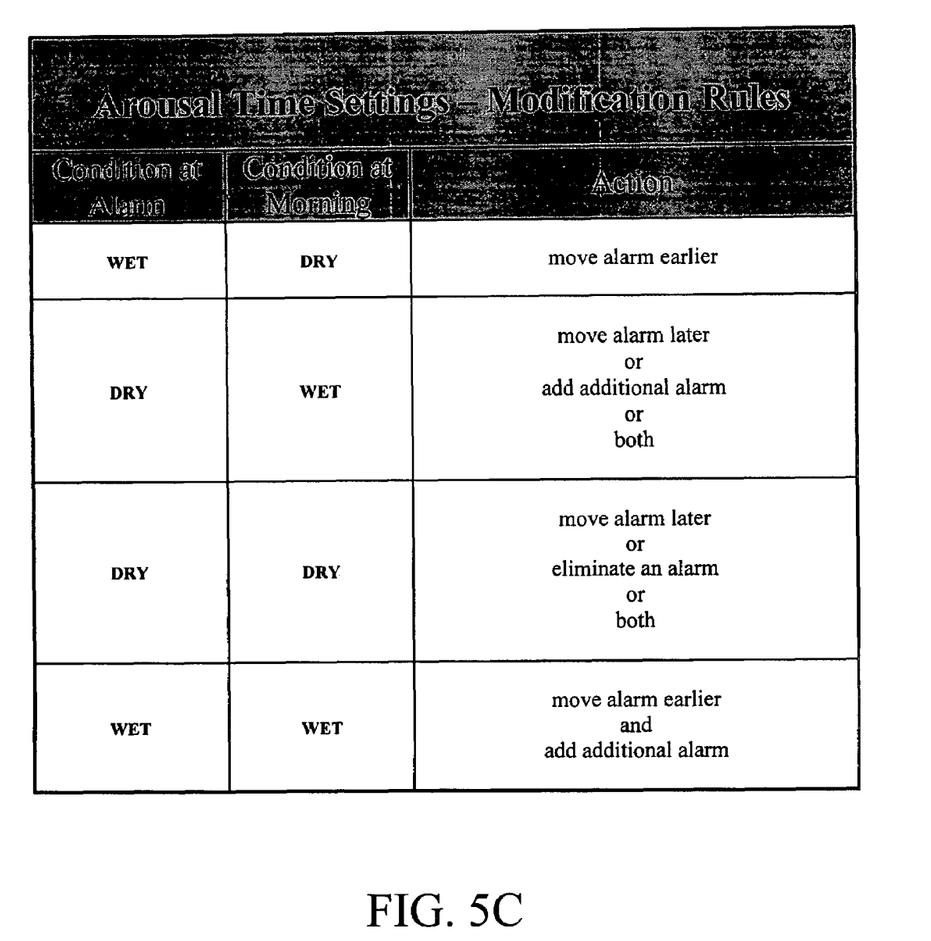
FIG. 5C is a table of the time setting modification rules of the method of the present invention.
Figure 6A:
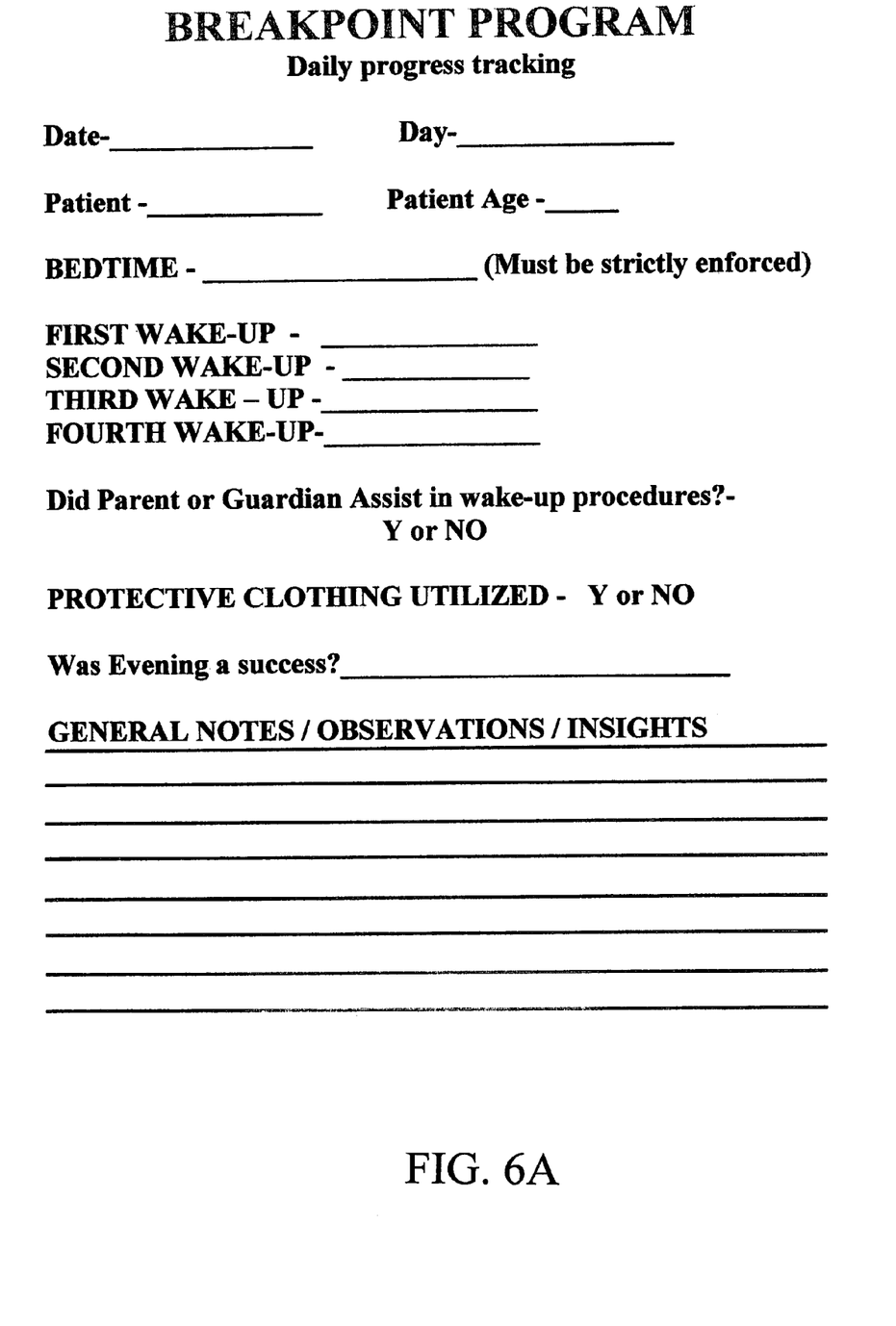
FIG. 6A is a blank form daily progress tracking chart for use with the bedwetting elimination system of the present invention.
Figure 6B:
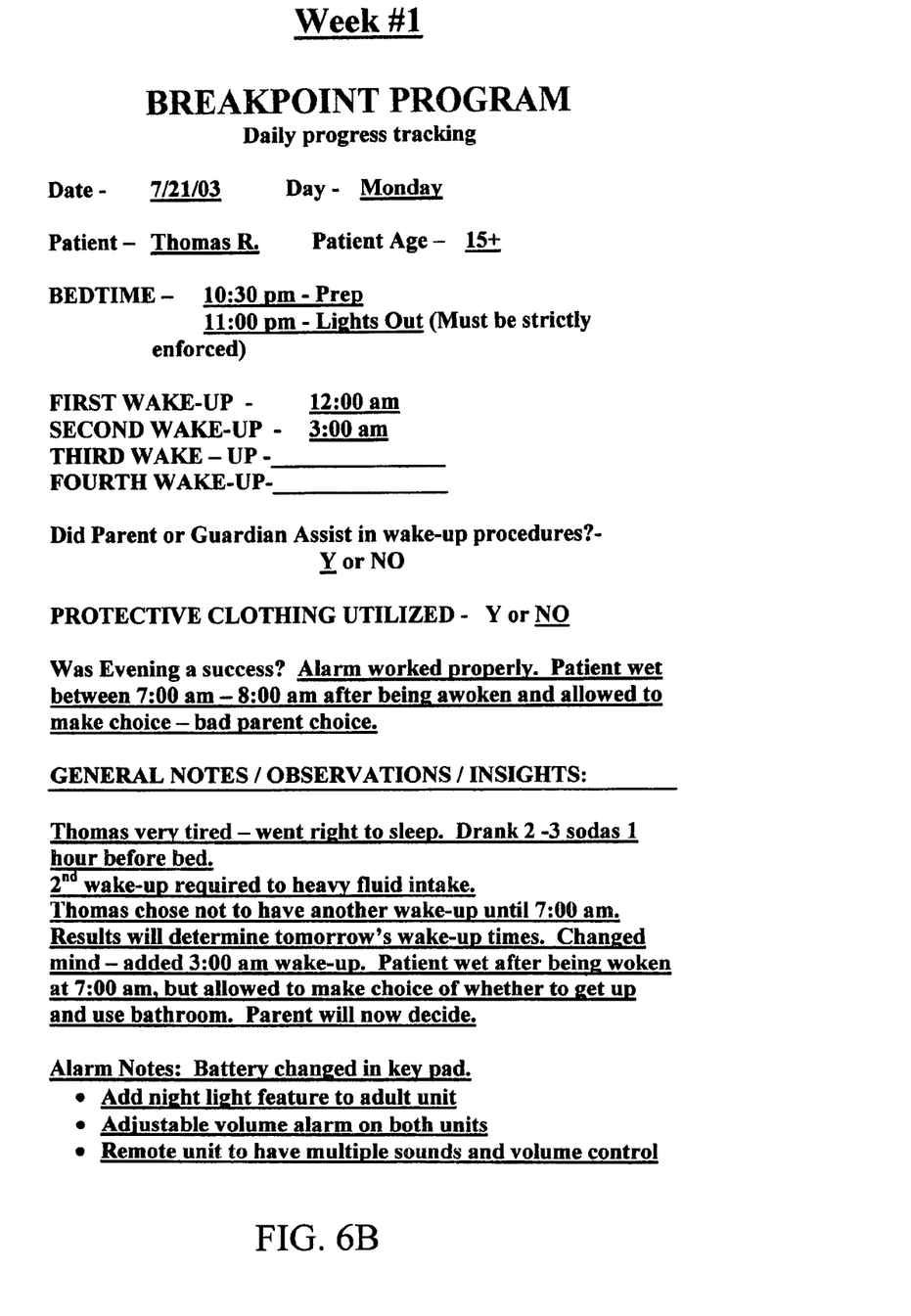
FIG. 6B is a first example of a completed daily progress tracking chart used with the bedwetting elimination system of the present invention.
Figure 6C:
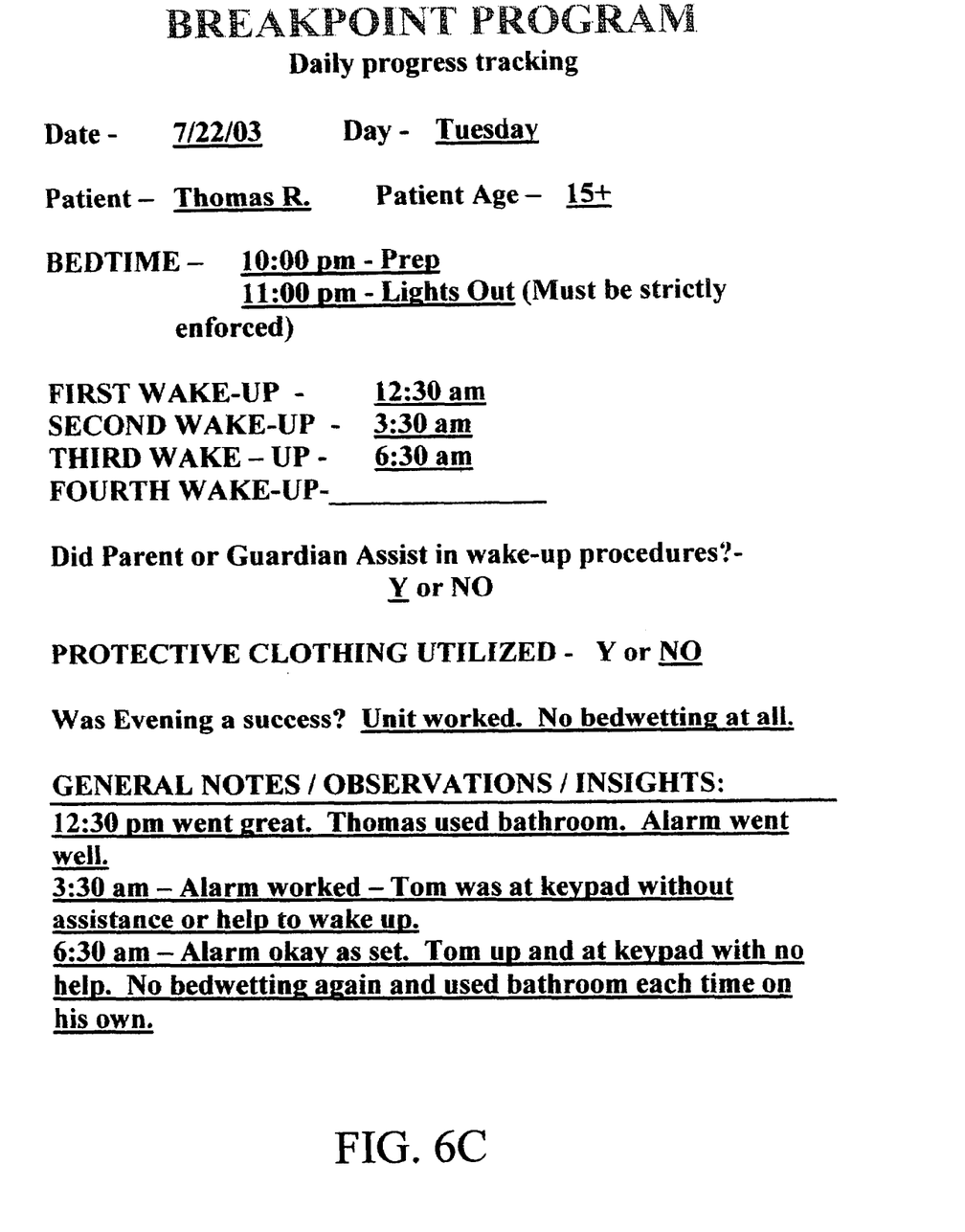
FIG. 6C is a second example of a completed daily progress tracking chart for use with the bedwetting elimination system of the present invention.
Figure 6D:
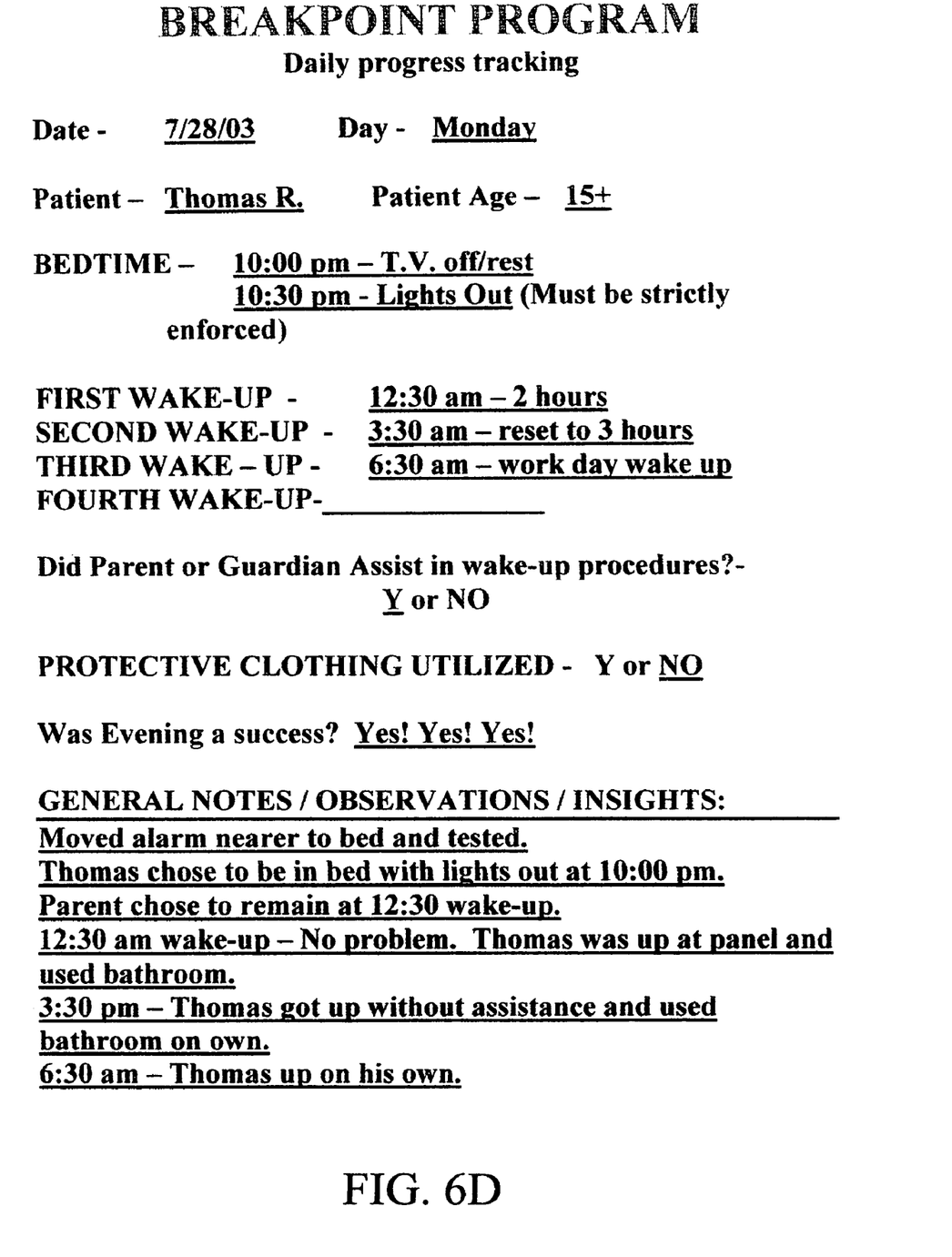
FIG. 6D is a third example of a completed daily progress tracking chart for use with the bedwetting elimination system of the present invention.

FIG. 5B summarizes the overall program methodology. The program is initiated (step 90), as described above, by establishing a user bedwetting pattern (step 92). Based on this pattern, the parent or caregiver programs the appropriate arousal times and operates the nightly sequence (step 94). If the arousal times remain appropriate (step 96) then the programmed arousal times are maintained (step 100). If not (step 96), a modification of the arousal time(s) is made (step 98) (according to the modification rules shown in FIG. 5C) and programmed (step 94) into the base unit. Alarm volume is progressively reduced through multiple nightly sequences (step 102). If a two week (preferred) program time period has elapsed (step 103) the nightly sequences are terminated (step 104). If not, or if consistent "dry arousal" events do not occur, the program is continued by a return to step 94.

Key to the success of this bedwetting elimination program is the user's desire to eliminate the bedwetting and to take responsibility for his or her behavior. The user must understand that the program is for their benefit and that they must be a part of the solution and really want to control or eliminate the problem. During the initial establishment of the program, dry clothing and bedding must be readily available for use during the night in order to minimize disturbance of sleep time. A plastic bag should be available to hold wet garments and bedding during the night. In the morning, the user should be required to launder their clothes and bedding.

In the event that the user cannot remember the character code sequence, a secondary code location should be established in the bathroom whereby the code is written down and accessible. The caregiver should not assist the user beyond waking up. The user must enter the code himself and remember where the code is written down if he forgets the code.

For certain users, the alarm may have to be set at a very loud level to ensure that the user is awakened. Although this may waken other individuals in the house, such inconvenience should be tolerated. Objections and non-support will only lengthen the timeline of the program or force the user to suspend the implementation of the program.

The multi-character code should be changed every three days to ensure that the user awakens to the point of mental consciousness. Forgetting the code is acceptable as long as the written code is available at a backup location. A night light in the bathroom is therefore a requirement of the program. It is also important to provide for a gradual decrease in the volume of the alarm (step 102). If after a two week period of time the program appears to be successful (step 103), the nightly sequences may be terminated (step 104). If some uncertainty as to success remains, the program may be continued (step 94).

Although the present invention has been described in terms of the foregoing preferred embodiments, this description has been provided by way of explanation only, and is not intended to be construed as a limitation of the invention. Those skilled in the art will recognize modifications of the present invention that might accommodate specific individuals. Such modifications as to implementation details do not depart from the spirit and scope of the invention which is further defined by the following claims.

I claim:

1. A system for use in facilitating the elimination of bedwetting behavior, the system comprising:
    a base unit having a clock/timer and means for programming scheduled arousal times based upon an established user's bedwetting pattern, the base unit further comprising means for transmitting a signal at the arousal times;
    an alarm unit for receiving the signal and activating an alarm for arousal of the user; and
    an alarm silence unit positioned in a location remote from the user for deactivation of the alarm, wherein the user must carry out a specified sequence of actions with the alarm silence unit in order to deactivate the alarm.

2. The system of claim 1 wherein the base unit is connected to the alarm unit through a wired communication line and the alarm silence unit is connected to the alarm unit through a wired communication line and the signal is communicated between the units by way of the wired communication lines.

3. The system of claim 1 wherein the base unit is connected to the alarm unit by a wireless communication link and the alarm unit is connected to the alarm silence unit by a wireless communication link and the signal is communicated between the units by way of the wireless communication links.

4. The system of claim 1 wherein the alarm silence unit comprises a keypad and the specified sequence of actions comprises pressing a specified sequence of keys on the keypad.

5. The system of claim 1 wherein the alarm silence unit further comprises means for changing the specified sequence of actions required to deactivate the alarm.

6. The system of claim 1 wherein the alarm activated at the alarm unit comprises an audible alarm.

7. The system of claim 1 wherein the alarm activated at the alarm unit comprises a visual alarm.

8. The system of claim 1 wherein the alarm unit further comprises a nightlight, the nightlight activated in conjunction with the activation of the alarm.

9. A method for facilitating the elimination of bedwetting behavior of a user, the method comprising the steps of:
    establishing arousal times coinciding with the bedwetting pattern of the user;
    awaking the user with an alarm at the established arousal times; and
    requiring the user to go to a remote location in order to deactivate the alarm, the user being required to carry out a specified sequence of actions in order to deactivate the alarm.

10. The method of claim 9 further comprising repeating the steps of awaking the user and requiring the user to go to a remote location in order to deactivate the alarm at least one time during a night.

11. The method of claim 9 further comprising the step of programming an alarm unit with the established arousal times the alarm unit positioned in proximity to the user.

12. The method of claim 9 further comprising the steps of:
    monitoring changes in the bedwetting pattern of the user; and
    modifying the established arousal times to continue to coincide with the bedwetting pattern of the user.

13. The method of claim 9 further comprising the step of progressively reducing a magnitude of the alarm through multiple repetitions of the method steps.

14. The method of claim 9 further comprising the step of providing a written record of the specified sequence of actions required to deactivate the alarm and positioning the written record at the remote location for reference by the user if necessary to deactivate the alarm.

15. The method of claim 9 further comprising the steps of recording on a written record nightly activities associated with carrying out the method steps and modifying a frequency of repetition for the method steps based upon modified behavior reflected in the written record.

* * * * *